United States Patent [19]

Rubinsky et al.

[11] Patent Number: 5,654,279
[45] Date of Patent: Aug. 5, 1997

[54] TISSUE DESTRUCTION IN CRYOSURGERY BY USE OF THERMAL HYSTERESIS

[75] Inventors: Boris Rubinsky, Albany; Amir-Homayoon Koushafar, Richmond, both of Calif.

[73] Assignee: The Regents of the University of California, Oakland, Calif.

[21] Appl. No.: 625,074

[22] Filed: Mar. 29, 1996

[51] Int. Cl.$^6$ .......................... A61K 38/02; A61K 38/17; A61B 17/36

[52] U.S. Cl. .................. 514/21; 514/8; 606/20; 606/21; 128/DIG. 27

[58] Field of Search .................. 514/8, 12, 2, 21; 606/20, 22, 23, 21; 424/9.3; 128/653.2, 653.1, DIG. 128

[56] References Cited

U.S. PATENT DOCUMENTS

| | | | |
|---|---|---|---|
| 4,531,373 | 7/1985 | Rubinsky | 62/63 |
| 5,147,355 | 9/1992 | Friedman et al. | 606/23 |
| 5,358,931 | 10/1994 | Rubinsky et al. | 514/12 |
| 5,437,673 | 8/1995 | Raust et al. | 606/23 |
| 5,531,742 | 7/1996 | Barken | 606/21 |

OTHER PUBLICATIONS

Gary M. Onik, "Ultrasound–Guided Cryosurgery," *Scientific American Science & Medicine*, Jan./Feb. 1996, pp. 62–71.

*Primary Examiner*—Jeffrey E. Russel
*Assistant Examiner*—Kathleen Carroll
*Attorney, Agent, or Firm*—Townsend and Townsend and Crew LLP

[57] ABSTRACT

Cell and tissue destruction by cryoablation is enhanced by the perfusion of the cells with thermal hysteresis proteins prior to the cryogenic freezing. The effect of the proteins is to promote the growth of spicular ice crystals in the intracellular fluid which destroy the cell by piercing the cell membrane. This decreases the incidence of cell preservation by freezing, thereby permitting a more uniform and controllable destruction of undesirable tissue by the cryoablation technique.

14 Claims, No Drawings

TISSUE DESTRUCTION IN CRYOSURGERY BY USE OF THERMAL HYSTERESIS

This invention lies in the heretofore unrelated fields of cryosurgery and the properties and uses of thermal hysteresis proteins.

BACKGROUND OF THE INVENTION

Cryosurgery has achieved wide acceptance as a clinical procedure and is proving useful for a rapidly increasing range of applications. Among these are the extraction of cataractous lenses of the eye, the repair of detached retinas, the ablation of heart tissue to correct cardiac arrhythmias, and the destruction of tumors in the prostate, liver, brain, and other internal organs. Cryosurgery involves the insertion of a cryoprobe to destroy undesired tissue by highly localized freezing. Once the tissue is frozen, it is allowed to thaw. The body's immune system then gradually decomposes the destroyed tissue and removes it from the body. Cryosurgery offers a number of advantages, including the fact that it is only minimally invasive yet highly controllable, and not dose limited.

Cryoprobes are thin, cylindrical devices that are cooled internally with a cryogen and insulated except at the tip. As the cryogen is circulated through the probe, freezing of the tissue occurs from the tip outward, producing a moving freezing front, or interface between frozen and nonfrozen tissue, that is sharply defined and propagates slowly through the tissue (at rates on the order of millimeters per minute). Relatively large regions can be treated with small probes; a 3-mm diameter probe for example can produce an ice ball 3.5 cm in diameter. When the region of pathological tissue is large and complex in shape, a frozen region corresponding closely to the tissue of interest can be generated by using several probes simultaneously. Multiple sites can be treated either separately or together. Since the insertion of the cryoprobes is the only physical invasion of the tissue, the complications entailed by the procedure and patient morbidity are reduced, and the procedure entails less distress to and disfiguration of the patient, all while achieving the therapeutic result at a lower cost than traditional invasive surgery.

One of the limitations of cryosurgery is the danger of freezing less than all of the undesired tissue, or the freezing of a substantial amount of healthy tissue adjacent to the undesired tissue. With recent advances in non-invasive medical imaging technology, however, under-freezing and over-freezing are much less of a danger. Intraoperative ultrasound imaging, for example, can be used to monitor the location of the freezing front and hence the size, shape and location of the frozen tissue, by virtue of the change in acoustic impedance between frozen and unfrozen tissue. Magnetic resonance imaging has also been used effectively, and offers the advantage of imaging the location of the freezing front in three dimensions with a resolution of 200 μm.

Imaging has revealed a further limitation, however: the freezing of living cells under certain conditions can preserve the cells rather than destroy them. An explanation of when preservation occurs rather than destruction and vice versa is found in the "two factor" (i.e., chemical and mechanical) theory proposed by Mazur, P., in "Cryobiology: The Freezing of Biological Systems," Science 168:939–949 (1970). This theory recognizes that the probability for an ice crystal to form at any given temperature is a function of volume, with the probability being higher in a larger volume. In a cellular suspension, the result of this effect is that ice will form first in the extracellular space since this space is much larger than the volume inside an individual cell. As the extracellular ice forms, the concentration of solutes in the remaining unfrozen solution rises, surrounding the cells with a hypertonic solution. This occurs while the intracellular fluid is still in liquid form, creating a chemical potential across the cell membrane. This causes water to pass through the membrane from the cell interior outward, leaving ions and organic solutes (to which the membrane is impermeable) inside the cell. The cell thus dehydrates and becomes hypertonic itself, which leads to cell death by chemical damage. Chemical damage however is a function of time and temperature, and water transport across the cell membrane is a rate-dependent process. Thus, lower cooling rates will increase the probability of chemical damage by allowing more time for exposure of the cell to hypertonic conditions. Conversely, ice formation within the cell itself is believed to cause cell death by mechanical damage, and increasing the cooling rate above a certain level causes ice nucleation inside the cell before the water can migrate outward. In the high cooling rate regime, therefore, the probability for intracellular ice formation and the consequential cell death increases, rather than decreases, with increasing cooling rate. The two conflicting modes of cell destruction result in a inverse U-shaped curve for the cell survival rate vs. the cooling rate. In addition to the cooling rate, other factors thought to affect the cell survival rate are the temperature gradient, the speed at which the freezing interface advances, the final freezing temperature, the holding time at that temperature, the warming rate subsequent to freezing, and the number of freeze-thaw cycles involved.

In cryosurgery, these parameters are particularly difficult to control since temperature control is achieved only at the tip of the probe and the composition of the surrounding tissue is not necessarily uniform. Variations in one or more of the freezing parameters will occur throughout the treated area during the course of a single procedure, since the continuously increasing size of the frozen region causes different parts of the tissue to experience different cooling rates, different final freezing temperatures and different holding times, depending on the distance of these parts from the probe tip. In addition, the manner of performing the procedure will vary between physicians as well as between clinics. As a result, the outcome of the typical cryosurgical procedure is often unpredictable and difficult to control.

SUMMARY OF THE INVENTION

It has now been discovered that cell destruction by cryosurgery can be achieved in a manner that is independent of cooling rate, final freezing temperature, and related thermal history parameters, by first perfusing the cells with one or more thermal hysteresis proteins, then freezing the cells with a cryogenic probe while the cells remain perfused with the protein. This procedure utilizes the protein's ability to control the manner and direction of ice crystal growth, and this invention resides in part in the discovery that this action of the proteins supersedes other factors affecting the rate, mechanism and location of crystal formation. The proteins achieve this effect by promoting and restricting the ice crystal growth in the cell interiors to spicular ice crystals. These crystals cause cell death by mechanical destruction of the cell, and they insure that this effect takes place over the entire range of cooling conditions, eliminating the need to rely on chemical damage over portions of the range.

These and other features and advantages of the invention will become apparent from the description that follows.

DETAILED DESCRIPTION OF THE INVENTION AND PREFERRED EMBODIMENTS

The existence of naturally-occurring macromolecular species known as "antifreeze proteins," "thermal hysteresis proteins," "antifreeze glycoproteins," and "antifreeze polypeptides" is well known and widely reported in the literature. The discovery of antifreeze glycoproteins, for example, was first reported by DeVries, A. L., et at., in "Freezing Resistance in Some Antarctic Fishes," Science 163:1073–1075 (7 Mar. 1969). DeVries et al. observed that various species of fish surviving in water at temperatures averaging −1.87° C. over the course of a year did so despite having insufficient levels of sodium chloride and other low molecular weight substances in their blood to depress the freezing point by conventional freezing point depression. DeVries et al. were able to attribute the survival of these species to the presence of certain glycosylated proteins having molecular weights ranging from about 2,500 to about 34,000, which are now referred to as antifreeze glycoproteins or "AFGPs." Further investigations revealed that many species of north temperate and Arctic fishes carry antifreeze compounds in their blood. Some of these compounds are glycoproteins while others contain no sugar moieties and are referred to as antifreeze polypeptides or proteins ("AFPs"), with molecular weights ranging from about 3,300 to about 12,000. Furthermore, while the compounds lower the freezing point, the melting point remains unaffected, hence the term "thermal hysteresis proteins."

Antifreeze proteins and glycoproteins have been isolated from a wide variety of sources, and these sources and the structures of the various proteins obtained from them have been reported extensively in the literature. The sources of these proteins include both fish species and non-fish species, and are listed in Tables I and II below.

TABLE I

THERMAL HYSTERESIS PROTEINS OF FISH SPECIES

| Protein Type, Composition and Size | Source Fish Species | Trivial Name of Fish species |
|---|---|---|
| Antifreeze glycoproteins (AFGPs): containing alanine, threonine and Gal-GalNAc disaccharide: M.W.: 2,700–36,000 | Antarctic notothenioids: *Pagothenia borchgrevinki* *Trematomus borchgrevinki* *Trematomus bernachii* *Dissostichus mawsoni* | Antarctic cod |
|  | Northern ocean gadoids: *Gadus agac* *Gadus morhua* *Microgadus tomcod* *Boreogadus saida* *Eligenus gracilis* | Greenland cod Atlantic cod Atlantic tomcod Arctic polar cod Saffron cod |
| Antifreeze Polypeptides (AFPs), Type I: alanine-rich; M.W.: 3,000–5,000 | Righteye flounders: *Pseudopleuronectus americanus* *Limanda ferruginea* | Winter flounder Yellowtail flounder |
|  | Cottids: *Myoxycephalus scorpius* *Myoxycephalus aenaeus* *Myoxycephalus scorpiodes* | Shorthorn sculpin Grubby sculpin Arctic sculpin |
| Antifreeze Polypeptides (AFPs), Type II: cysteine-rich; homologous to C-type lectins; M.W.: 12,000 | Cottid: *Hemitripterus americanus* *Osmerus mordex* *Clupea harengus harengus* | Sea raven Smelt Herring |
| Antifreeze Polypeptides (AFPs), Type III: | Eel pouts: *Macrozoarces americanus* | Ocean pout |

TABLE I-continued

THERMAL HYSTERESIS PROTEINS OF FISH SPECIES

| Protein Type, Composition and Size | Source Fish Species | Trivial Name of Fish species |
|---|---|---|
| no cysteines, and not rich in alanines; M.W.: 6,000 | *Rhigophila dearborni* *Lycodes polaris* | Antarctic eel pout Arctic eel pout |

TABLE II

NON-FISH SOURCES OF THERMAL HYSTERESIS PROTEINS

| | Species |
|---|---|
| A. Insects Other Than Beetles: Order | |
| Collembola | 7 spp. |
| Plecoptera | *Arcynopteryx compacta* |
| Orthoptera | *Parcoblata pennsylvanica* |
| Hemiptera | *Oncopeltus fasciatus* |
| Mecoptera | *Boreus westwoodi* |
| Lepidoptera | *Choristoneura fumiferana* |
| B. Coleoptera (Beetles): Family | |
| Tenebrionidae | *Tenebrio molitor* *Meracantha contracta* *Uloma impressa* *Platydema sp.* |
| Elateridae | *Ampedus lineatus* *Ampedus sp.* *Lepidotus discoideus* *Melanotus sp.* |
| Cucujidae | *Cucujus clavipes* |
| Pyrochridae | *Dendroides canadensis* |
| Lampyridae | *Photinus sp.* |
| Coccinellidae | *Coccinella novemnotata* |
| Scolytidae | *Ips acuminatus* |
| Cerambycidae | *Rhagium inquisitor* |
| C. Non-Insect Arthropods: Animal | |
| Spiders | *Philodromus sp.* *Clubiona sp.* *Bolyphantes index* |
| Centipede | *Lithobius forficatus* |
| Mite | *Alaskozetes antarcticus* |
| D. Other Invertebrates: | |
| Mussel | *Mytilus edulis* |

The proteins which have been the most extensively studied, and which are the preferred proteins for use in the practice of the present invention, are those isolated from fish species. As indicated in Table I, these proteins include both glycosylated proteins (AFGPs) and non-glycosylated proteins (AFPs), and the latter fall within three general categories, designated in the literature and known among those skilled in the art as Type I, Type II, and Type III.

The AFGPs generally consist of a series of repeats of the tripeptide unit alanylthreonyl-alanyl, with the disaccharide β-D-galactosyl-(1→3)-α-N-acetyl-D-galactosamine attached to the hydroxyl group of the threonine residue, although variations exist. For example, AFGPs of relatively low molecular weight contain proline and arginine residues in place of some of the alanine and threonine residues, respectively. Chromatographic studies of the AFGPs from representative fish species have revealed eight major molecular weight fractions, as indicated in Table III.

TABLE III

Molecular Weight Fractons of AFGPs
From *Pagothenia borchgrevinki*

| Fraction No. | Molecular Weight |
| --- | --- |
| 1 | 33,700 |
| 2 | 28,800 |
| 3 | 21,500 |
| 4 | 17,000 |
| 5 | 10,500 |
| 6 | 7,900 |
| 7 | 3,500 |
| 8 | 2,600 |

The AFPs differ from one another to a larger degree than do the AFGPs. As indicated in Table I, the three types of AFPs differ from each other in their residue content. Type I AFPs are rich in alanine residues (about 65%), with most of the remainder consisting of polar residues such as aspartic acid, glutamic acid, lysine, serine and threonine. The molecular weight ranges from about 3,300 to about 6,000. Type II AFPs are considered to be rich in cysteine (actually half-cysteine) residues, and are homologous to C-type lectins. Type II AFPs from the sea raven contain 7.6% cysteine, 14.4% alanine, 19% total of aspartic and glutamic acids, and 8% threonine. The molecular weight ranges from about 14,000 to about 16,000. Type III AFPs are devoid of cysteine residues and not rich in alanine residues. No conspicuous dominance of any particular amino acid is evident, and the amino acid content is evenly divided between polar and non-polar residues. The molecular weight ranges from about 5,000 to about 6,700. All percents referred to in this paragraph are on a mole basis.

Antifreeze proteins from insects are primarily AFPs of Type II, and typical compositions in terms of amino acid residues are those of the *Choristoneura fumiferana* (spruce budworm) and *Tenebrio molitor* (beetle). These are listed in Table IV, which also includes the amino acid composition of the sea raven for comparison.

TABLE IV

Comparative Amino Acid Compositions of Type II AFPs

| Amino Acid Residue | Spruce Budworm Fraction II | Beetle | Sea Raven |
| --- | --- | --- | --- |
| Asx | 9.5 | 5.3 | 10.7 |
| Thr | 6.0 | 2.3 | 7.9 |
| Ser | 13.0 | 11.1 | 8.2 |
| Pro | 5.0 | 0.0 | 6.7 |
| Glx | 11.0 | 12.4 | 9.1 |
| Gly | 15.0 | 11.4 | 8.1 |
| Ala | 8.0 | 5.0 | 14.4 |
| ½-Cys | 6.0 | 28.0 | 7.6 |
| Val | 3.0 | 2.3 | 1.2 |
| Met | 0.0 | 0.0 | 5.4 |
| Ile | 1.2 | 1.0 | 1.7 |
| Leu | 6.5 | 2.2 | 6.2 |
| Tyr | 1.0 | 0.0 | 1.2 |
| Phe | 2.2 | 0.0 | 2.0 |
| Lys | 3.1 | 15.4 | 2.1 |
| His | 0.0 | 3.1 | 2.5 |
| Trp | 0.0 | 0.0 | 2.8 |
| Arg | 8.0 | 0.0 | 2.3 |

Antifreeze proteins and glycoproteins can be extracted from the sera or other bodily fluids of fish or insects by conventional means. Isolation and purification of the proteins is readily achievable by chromatographic means, as well as by absorption, precipitation, and evaporation. Other methods, many of which are described in the literature, will be readily apparent to those skilled in the art.

Thermal hysteresis proteins may also be produced synthetically, either by conventional chemical synthesis methods or by methods involving recombinant DNA. The DNA coding sequences of the genes which form these proteins have been elucidated and are extensively reported. See, for example, DeVries, A. L., et al., J. Biol. Chem. 246:305 (1971); Lin, Y., et al., Biochem. Biophys. Res. Commun. 46:87 (1972); Yang, D. S. C., et al., Nature 333:232 (1988); Lin, Y., Proc. Natl. Acad. Sci. U.S.A. 78:2825 (1981); Davies, P. L., et al., J. Biol. Chem. 79:335 (1982); Gourlie, B., et al., J. Biol. Chem. 259:14960 (1984); Scott, G. K., et at., Can. J. Fish. Aquat. Sci. 43:1028 (1986); Scott, G. K., et al., J. Mol. Evol. 27:29 (1988). Successful microinjection of the AFP gene into species other than its native species has also been reported. See, for example, Zhu, Z., et al., Angew. Ichthyol. 1:31 (1985); Chourrout, D., et al., Aquaculture 51:143 (1986); Dunman, R. A., et al., Trans. Am. Fish. Soc. 116:87 (1987); Fletcher, G. L., et al., Can. J. Fish Aquat. Sci. 45:352 (1988); MacLean, N. D., et at., Bio Technology 5:257 (1987); Smart, G. W., et at., Development 103:403 (1988); McEvoy, T., et al., Aquaculture 68:27 (1988); Ozato, K, et al., Cell Differ. 19:237 (1986).

Thermal hysteresis proteins of particular interest in this invention are those that are relatively low in molecular weight, such as those having molecular weights within the range of about 2,000 to about 10,000, preferably about 2,600 to about 6,000, and most preferably about 3,000 to about 4,000.

In the practice of this invention, the thermal hysteresis proteins are most conveniently administered in liquid form, as a solution or suspension in a fluid that is tissue-compatible. Aqueous solutions or solutions in physiological saline (approximately 0.9% sodium chloride (weight/volume) in water) are preferred. For best results, the concentration of the protein in the solution or suspension will generally range from about 1 mg/mL to about 30 mg/mL, preferably from about 1 mg/mL to about 20 mg/mL, and most preferably from about 5 mg/mL to about 15 mg/mL. Administration can be achieved by injection into the tissue of interest by syringe, ingestion, perfusion of an organ of interest through the vasculature, or other means of saturating and equilibrating the tissue with the dissolved protein.

Once the tissue is perfused with thermal hysteresis protein, cryoablation of the tissue is performed according to known techniques. A cryogenic probe is advanced to the center of the tissue, or a combination of two or more probes are placed at selected locations inside the tissue to form a cooling region conforming to the contours of the tissue to be ablated. The probe is fully enclosed with multiple lumens to permit the circulation of a supercooled fluid to the distal tip and back. Liquid nitrogen is commonly used as the supercooled fluid, boiling inside the tip of the cryoprobe at −196° C. The boiling produces a film of insulating gas between the liquid nitrogen and the metal shell of the cryoprobe, and the metal shell limits the lowest temperature around the microprobe to about −160° C. With the tip at −160° C., a tissue temperature of −20° C. or lower is achieved out to about 2 cm from the probe surface. Probes of this general description are well known in the art and widely disclosed in the literature, including U.S. Pat. No. 5,147,355, to Friedman et al. (Brigham and Womens Hospital, Boston, Mass., USA, Sep. 15, 1992) and U.S. Pat. No. 5,437,673, to Baust et al. (Cryomedical Sciences, Inc., Rockville, Md., USA, Aug. 1, 1995), both of which are incorporated herein by reference.

Cryogenic probes in the practice of this invention are preferably used in combination with simultaneous imaging techniques, notably ultrasound and magnetic resonance imaging. These techniques are used in the conventional manner, and their use does not interfere with the operation of the cryogenic probes. Ultrasound imaging, for example, can be performed in either two dimensions or three dimensions, the latter by computer reconstruction of two-dimensional ultrasound data into a three dimensional image. Ultrasound imaging is achieved by placement of an ultrasound transducer at a location close to the tissue of interest. For prostate imaging, for example, the ultrasound transducer can be placed transrectally. For the liquid-nitrogen cryoprobe discussed above, the region of tissue where the temperature is below −20° C. is surrounded by a rim approximately 3 mm thick within which the temperature rises to 0° C. The ultrasound image of this rim is a bright echo. In magnetic resonance imaging is performed without a transducer placed adjacent to the cryoprobe. Frozen tissue appears black on an MRI scan since it produces no signal at all, and since the remainder of the image is not affected by the frozen zone, the full extent of the frozen zone is detectable.

Further descriptions of the use of these imaging methods are found in the following publications, each of which is incorporated herein by reference:

Onik, G., et al., "Ultrasound-guided hepatic cryosurgery in the treatment of metastatic colon carcinoma," Cancer 67(4):901–907 (1991)

Onik, G., et al., "Transrectal ultrasound-guided percutaneous radical cryosurgical ablation of the prostate," Cancer 72(4):1291–1299 (1993)

Rubinsky, B., "Cryosurgery imaging with ultrasound," Mechanical Engineering 108(3):48–51 (1986)

Rubinsky, B, et al., "Monitoring cryosurgery in the brain and prostate with proton NMR," Cryobiology 30:191–199 (1993)

The following examples are offered as illustration, and are not intended to limit or define or impose limits on the scope of the invention.

EXAMPLES

Materials and Methods

In the following examples, two important thermal variables, the cooling rate and the end temperature to which the cells are frozen, were investigated for their effect on the degree of damage to the cells. The cells were cultured human prostatic cancer cells of an adenocarcinoma cell line (ND-1) developed by Narayan, P., et al., "Establishment and characterization of a human primary prostatic adenocarcinoma cell line (ND-1)," J. Urol. 148(5):1600–1604 (1992), grown in Dulbecco's Modified Eagle's Medium (DMEM) supplemented with 10% fetal bovine serum, penicillin (100 units/mL) and streptomycin phosphate (100 mg/mL), in 75-cm$^3$ flasks incubated at 37° C. in a humidified 5% $CO_2$ atmosphere. Once the cells reached confluence, the growth medium was aspirated and 3 mL of 0.05% trypsin was added to detach the cells from the flask. The resulting cell suspension was centrifuged to allow aspiration of the trypsin, and the cells were resuspended in buffered physiological saline. Approximately 50 μL of the saline cell suspension was placed on microscope slides with specially designed silicon wells to contain the suspension.

Freezing and observation of the cells were then performed on an apparatus which is termed a "directional solidification stage" and which permits accurate control of all thermal variables. The apparatus is described in Rubinsky, U.S. Pat. No. 4,531,373, issued Jul. 30, 1985, which is incorporated herein by reference. The apparatus consists of a pair of copper blocks positioned adjacent to each other with flat heat transfer surfaces in a common plane separated by a gap 3 mm in width. Each block contains a passage for coolant flow, a resistance heater, and a thermocouple, and the optical path of a microscope passes through the gap. A microscope slide is placed across both heat transfer surfaces and is moved at a constant velocity along the surfaces by a stepper motor, passing over the gap and intersecting the optical path of the microscope. The blocks are maintained at preselected temperatures by the coolant and heaters, one block being maintained above the freezing temperature of a given specimen and the other below the freezing temperature, the arrangement resulting in a linear temperature gradient across the gap. A specimen is placed on the slide, and the slide is initially positioned with the specimen above the warmer of the two blocks. The slide is then moved in the direction of the cooler block by the stepper motor, causing the specimen temperature to drop in accordance with the position of the specimen relative to the two blocks. As a result, the temperature gradient across the specimen, the temperature range experienced by the specimen, the freezing front velocity and the cooling rate are controlled to a high degree of accuracy. Once the sample has reached the low-temperature block, the sample is held at the low temperature for a prescribed period of time. The specimen is then rewarmed by translating the slide with the sample from the cold block back to the warm block at a controlled velocity. When thin samples are used, this apparatus makes it possible to view the cells through the microscope and thereby observe the changes occurring in the cells as they freeze and thaw.

Example 1

This example illustrates the freezing of cancer cells in the absence of thermal hysteresis proteins.

In this study, the high-temperature block of the directional solidification stage was maintained at 37° C. and the cold-temperature block at temperatures between −5° C. and −40° C. The velocity of movement between the blocks was set to achieve cooling rates of 1° C./min, 5° C./min and 25° C./min, which are typical of cooling rates in frozen tissue at the locations of the freezing fronts in cryoablation procedures. Once the samples had reached the lowest temperature, they were held at that temperature for five minutes, then rapidly returned to the warm block. Two sets of experiments were performed: in one set the cells were exposed to only one freeze-thaw cycle, and in the other the cells were exposed to two identical freeze-thaw cycles. Thus, at least three experiments were performed for each experimental condition.

The viability of thawed cells and of controls that had not undergone freezing was evaluated with a trypan blue test and a two-color fluorescence cell viability assay. In the trypan blue test, membrane integrity was assessed by mixing a cell suspension with an equal volume of a 0.3% trypan blue solution. A count of viable (non-stained) vs. nonviable (stained) cells was then obtained by hemocytometer. The two-color fluorescence cell viability assay determined the ratio of live to dead cells based on intracellular esterase activity and plasma membrane integrity. A test kit, supplied by Molecular Probes, Inc., Eugene, Oreg., USA, was used, which contained the cell permeant calcein AM and the membrane-impermeant ethidium homodime (EthD-1). In live cells, calcein AM undergoes enzymatic conversion to fluorescent calcein, producing an intense uniform green (about 530 nm) fluorescence. Cells with damaged membranes are marked by the EthD-1, which fluoresces after binding to nucleic acids, thereby producing a bright red (about 600 nm) fluorescence in dead cells, while being excluded by the intact plasma membrane of live cells.

The two-color fluorescence cell viability assay was performed by resuspending cells after freezing and thawing, and mixing 100 μL of the resuspended cells with 200 μL of the dye mix which contained 5 μL calcein AM, 10 μM of EthD-1 and less than 0.1% DMSO, in Dulbecco's phosphate buffered salt solution. The mixture was incubated at 37° C. for thirty minutes, then studied under a fluorescent microscope. The ratio of live to dead cells was determined by counting the dead and live cells from randomly selected sampled regions of stained cells using fluorescence microscopy. In both the trypan test and the two-color fluorescence cell viability assay, each cell count exceeded a total of 300 cells from randomly selected regions of a sample. Results from the two tests agreed within 3%-8%.

Using these methods, the ND-1 cell line was frozen to various end temperatures at various cooling rates, then thawed. The percentage of dead cells, normalized with respect to unfrozen controls, was then plotted as a function of the final temperature to which the cells were frozen, at cooling rates of 1° C./min, 5° C./min, and 25° C./min.

The plots corresponding to cooling rates of 1° C./min and 5° C./min indicated that in experiments where the final temperatures were between 0° C. and about −20° C. there was a gradual increase in cell death (from 13% to 87% for experiments performed at the rate of 1° C./min, and from 5% to 87% for experiments performed at the rate of 5° C./min) as the final freezing temperature dropped. In experiments where the final temperatures were below about −20° C., the percent cell destruction continued to increase but at a slower rate. At a final temperature of −40° C. in the 1° C./min tests, the average percent dead at −40° C. was 95%, while at the same final temperature in the 5° C./min tests, the average percent dead was 98%. For both cooling rates, therefore, the cells upon reaching −40° C. still had not been completely destroyed by the freezing process.

The plot representing tests performed at a cooling rate of 25° C./min showed a step increase in the percentage cell destruction between the final freezing temperatures of −5° C. and −15° C., and the destruction rates in different experiments was spread over a wide range of values in this temperature range. This indicates intracellular freezing, which is a statistical phenomenon that occurs within a narrow range of temperatures. The cell damage during freezing at the cooling rate of 25° C./min is therefore due to intracellular ice formation. Accordingly, the transition between chemical damage and damage due to intracellular ice formation in human prostate adenocarcinoma occurs somewhere between the cooling rates of 5° C./min and 25° C./min.

Example 2

This example illustrates the freezing of cancer cells in the presence of thermal hysteresis proteins.

Cellular suspensions of the same types of cells as those used in Example 1 were prepared. Some of the suspensions included a thermal hysteresis protein from *Pleuronectus americanus* with a molecular weight of 3,600 at a concentration of 10 mg/mL, while the remainder did not include any thermal hysteresis proteins. Drops of the suspensions were placed on glass slides in layers approximately 100 μm thick, covered with cover slips, and frozen on the directional solidification stage. In these experiments, the freezing process was recorded on videotape through a light microscope with a magnification of 40×. Several experiments were performed in which the cells were frozen at different cooling rates ranging from 1° C./min to 25° C./min.

In cell suspensions that did not contain thermal hysteresis proteins, large finger-like ice crystals formed during the freezing process. This indicates the rejection of solutes by the ice as it is formed. As freezing continued, the unfrozen cells were pushed into channels between the finger-like ice crystals. Since the extracellular fluid in the channels contains a high concentration of solutes (from solutes rejected by the ice crystals), the unfrozen cells will begin to dehydrate in an attempt to equilibrate the chemical potential between the intracellular and extracellular solutions, and be eventually damaged by intracellular chemical damage.

In cell suspensions that did contain the thermal hysteresis protein, the freezing resulted in the formation of very fine micron-size spicular ice crystals in the extracellular fluid. These crystals gradually deformed the unfrozen cells, causing the cell membranes to burst. Ice then engulfed the cell interiors which by then had become supercooled. The sudden freezing of the cell interiors produced many small ice crystals within each cell, causing the intracellular ice to appear as a dark image.

The distance between the advancing freezing front and the location at which intracellular freezing occurred was less than 200 μm, and the temperature at the locations where intracellular freezing occurred was above −2° C., as determined from the linear location of this freezing along the directional solidification stage. These small distances and small temperature differences indicate that the extent of cell damage conformed very closely to the extent of freezing, and that this occurred independently of the cooling rate or the end temperature.

Example 3

This example illustrates the freezing of prostate cancer tissue slices in the presence of thermal hysteresis proteins.

Human prostate tissue was obtained from needle biopsies of the normal and diseased parts of human prostates. The tissues to be studied were immersed in a preserving solution (Hank's balanced saline solution, obtained from Sigma Chemical Company, St. Louis, Miss., USA, to which penicillin G, streptomycin and gentamycin had been added), in some cases containing the thermal hysteresis protein from *Pleuronectus americanus* with a molecular weight of 3,600 at a concentration of 10 mg/mL, and in other cases with no thermal hysteresis protein present. The tissues were sliced to a thickness of about 300 μm with a microtome, placed on a glass slide and covered with a coverslip. The tissues were then placed on the directional solidification stage where they were subjected to freezing at the same cooling rates as in Example 2, and recorded by videotape through a light microscope.

After freezing and thawing, the viability of the cells was determined using the two-color fluorescence cell viability assay described in Example 1. In this series of tests, the tissue slices both before and after freezing were incubated in 250 μL of 10 μM EthD-1 in Dulbecco's phosphate buffer at 37° C. for thirty minutes with gentle rocking. As explained above, this dye fluoresces red upon binding to nucleic acids of compromised cells. After the incubation, SYTO™-16 (a nucleic acid stain from Molecular Probes, Inc., of Eugene, Oreg., USA, 250 μL, 10 μM) was added to the mix and incubated at 37° C. with gentle rocking for an additional 60 minutes. The latter stain is a cell-permeating dye with very high penetration ability and high affinity for nucleic acids, fluorescing a very bright green color (about 525 nm) upon binding to nucleic acids. Neither EthD-1 nor SYTO-16 interferes with the binding site of the other. By identifying those cells that fluoresce both green and red as compared to those that fluoresce only green, one can distinguish live cells from dead cells in intact tissue.

Using these procedures, the videotape indicated that the cells in the tissue slices immersed in solutions of the thermal hysteresis protein burst in the same manner and at the same stage of the freezing process as cells in the cell suspensions of Example 2. Such bursts were not observed in any of the tissue slices that had not been treated with the thermal hysteresis protein. This demonstrates the similarity in behavior between cells in suspension and those in tissue when treated with the thermal hysteresis protein.

The fluorescent dye tests performed after freezing and thawing showed that the cells in the tissue frozen in the presence of the thermal hysteresis protein were completely destroyed, while those frozen in the absence of the thermal hysteresis protein suffered only partial destruction for all the tested freezing conditions.

The foregoing is offered primarily for purposes of illustration. It will be readily apparent to those skilled in the art that the operating conditions, materials, step sequences and other parameters of the procedures described herein may be further modified or substituted in various ways without departing from the spirit and scope of the invention.

We claim:

1. A method for the therapeutic treatment of a living organism by destruction of undesirable tissue containing living cells with aqueous intracellular fluid, comprising:
   (a) perfusing said tissue with a solution containing from about 1 mg/mL to about 50 mg/mL of a thermal hysteresis protein in a tissue-compatible solvent; and
   (b) selectively freezing said tissue thus perfused by a cryogenic probe inserted therein and maintained therein for a sufficient period of time to mortally damage said cells by the formation of spicular ice crystals inside said cells.

2. A method in accordance with claim 1 in which said thermal hysteresis protein is a protein having the molecular structure of a thermal hysteresis protein isolated and purified from a polar fish species.

3. A method in accordance with claim 1 in which said thermal hysteresis protein is a protein having the molecular structure of a thermal hysteresis protein isolated and purified from a member selected from the group consisting of *Antarctic notothenioids*, northern ocean gadoids, righteye flounders, cottids and eel pouts.

4. A method in accordance with claim 1 in which said thermal hysteresis protein is a member selected from the group consisting of:
   (a) antifreeze glycoproteins isolated and purified from a member selected from the group consisting of *Pagothenia borchgrevinki, Trematomus borchgrevinki, Trematomus bernachii*, and *Dissostichus mawsoni*;
   (b) Type I antifreeze polypeptides isolated and purified from a member selected from the group consisting of *Pseudopleuronectus americanus* and *Limanda ferruginea*;
   (c) Type II antifreeze polypeptides isolated and purified from *Hemitripterus americanus*; and
   (d) Type III antifreeze polypeptides isolated and purified from a member selected from the group consisting of *Macrozoarces americanus, Rhigophila dearborni* and *Lycodes polaris*.

5. A method in accordance with claim 1 in which said thermal hysteresis protein is a member selected from the group consisting of:
   (a) antifreeze glycoproteins isolated and purified from a member selected from the group consisting of *Dissostichus mawsoni* and *Trematomus bernachii*;
   (b) Type I antifreeze polypeptides isolated and purified from *Pseudopleuronectus americanus*;
   (c) Type II antifreeze polypeptides isolated and purified from *Hemitripterus americanus*; and
   (d) Type III antifreeze polypeptides isolated and purified from *Macrozoarces americanus*.

6. A method in accordance with claim 1 in which said thermal hysteresis protein is an antifreeze polypeptide isolated and purified from *Pseudopleuronectus americanus*.

7. A method in accordance with claim 1 in which said thermal hysteresis protein has a molecular weight of from about 2,000 to about 10,000.

8. A method in accordance with claim 1 in which said thermal hysteresis protein has a molecular weight of from about 2,600 to about 6,000.

9. A method in accordance with claim 1 in which said thermal hysteresis protein has a molecular weight of from about 3,000 to about 4,000.

10. A method in accordance with claim 1 in which said solution contains from about 1 mg/mL to about 30 mg/mL of said thermal hysteresis protein.

11. A method in accordance with claim 1 in which said solution contains from about 5 mg/mL to about 15 mg/mL of said thermal hysteresis protein.

12. A method in accordance with claim 1 in which step (b) produces a frozen region of growing size defined by a moving interface between frozen and unfrozen tissue, said method further comprising monitoring the location of said interface by imaging.

13. A method in accordance with claim 12 in which said imaging is ultrasound imaging.

14. A method in accordance with claim 12 in which said imaging is magnetic resonance imaging.

* * * * *